United States Patent
Justin et al.

(10) Patent No.: US 10,456,143 B2
(45) Date of Patent: Oct. 29, 2019

(54) COMPOSITE JOINT ARTHROPLASTY SYSTEMS AND METHODS

(71) Applicant: Titanium Fusion Technologies, LLC, Orlando, FL (US)

(72) Inventors: Daniel F. Justin, Orlando, FL (US); Vuong binh nguyen, Windermere, FL (US); Dana J. Medlin, Omaha, NE (US)

(73) Assignee: Titanium Fusion Technologies, LLC, Orlando, FL (US)

( * ) Notice: Subject to any disclaimer, the term of this patent is extended or adjusted under 35 U.S.C. 154(b) by 38 days.

(21) Appl. No.: 15/625,802

(22) Filed: Jun. 16, 2017

(65) Prior Publication Data
US 2018/0250134 A1 Sep. 6, 2018

Related U.S. Application Data

(60) Provisional application No. 62/466,249, filed on Mar. 2, 2017.

(51) Int. Cl.
*B22F 7/00* (2006.01)
*A61B 17/15* (2006.01)
(Continued)

(52) U.S. Cl.
CPC .......... *A61B 17/154* (2013.01); *A61B 17/142* (2016.11); *A61B 17/155* (2013.01);
(Continued)

(58) Field of Classification Search
CPC .. A61F 2/38; B22F 7/064; B22F 7/062; B22F 7/06; B22F 2001/0033;
(Continued)

(56) References Cited

U.S. PATENT DOCUMENTS

| | | |
|---|---|---|
| 5,653,714 A | 8/1997 | Dietz et al. |
| 5,658,334 A | 8/1997 | Caldarise et al. |

(Continued)

FOREIGN PATENT DOCUMENTS

| | | |
|---|---|---|
| AU | 2003261497 B2 | 5/2004 |
| AU | 2004204267 B2 | 7/2004 |

(Continued)

OTHER PUBLICATIONS

Rapid Solid-State Synthesis of Titanium Aluminides, Richard G. Blair, Jan. 9, 2003.
(Continued)

*Primary Examiner* — Brian E Pellegrino
*Assistant Examiner* — Rebecca Lynee Zimmerman
(74) *Attorney, Agent, or Firm* — David Meibos; Maywood IP Law

(57) ABSTRACT

A prosthesis may have an articulating component formed via casting and a 3D printed bone anchoring component with a joint-facing side and a bone-facing side. The bone-facing side may have a bone engagement surface with a porous structure with pores selected to facilitate in-growth of the bone into the pores. The bone facing side may further have a surface layer of Titanium Dioxide nanotubes. The joint-facing side may be secured to the articulating component by melting Titanium nanoparticles at a temperature below the melting temperatures of the major constituents of the articulating component and/or the bone anchoring component, such as Cobalt, Chromium, and/or Titanium, so as to avoid significantly modifying the crystalline structures of the articulating component and/or the bone anchoring component. The melting temperature of the Titanium nanoparticles may be about 500° C.

12 Claims, 5 Drawing Sheets

(51) Int. Cl.
   *A61B 17/17* (2006.01)
   *A61F 2/38* (2006.01)
   *A61B 17/14* (2006.01)
   *A61B 17/16* (2006.01)
   *A61F 2/46* (2006.01)
   *A61F 2/30* (2006.01)
   *B33Y 10/00* (2015.01)
   *B33Y 80/00* (2015.01)
   *B22F 3/105* (2006.01)
   *B22F 7/08* (2006.01)
   *B22F 3/11* (2006.01)
   *B22F 7/06* (2006.01)

(52) U.S. Cl.
   CPC ........ *A61B 17/157* (2013.01); *A61B 17/1675* (2013.01); *A61B 17/1764* (2013.01); *A61F 2/30767* (2013.01); *A61F 2/30771* (2013.01); *A61F 2/38* (2013.01); *A61F 2/389* (2013.01); *A61F 2/3859* (2013.01); *A61F 2/461* (2013.01); *A61F 2/30744* (2013.01); *A61F 2002/305* (2013.01); *A61F 2002/30011* (2013.01); *A61F 2002/3038* (2013.01); *A61F 2002/3084* (2013.01); *A61F 2002/3092* (2013.01); *A61F 2002/3093* (2013.01); *A61F 2002/3097* (2013.01); *A61F 2002/30332* (2013.01); *A61F 2002/30448* (2013.01); *A61F 2002/30451* (2013.01); *A61F 2002/30604* (2013.01); *A61F 2002/30818* (2013.01); *A61F 2002/30841* (2013.01); *A61F 2002/30845* (2013.01); *A61F 2002/30878* (2013.01); *A61F 2002/30884* (2013.01); *A61F 2002/30968* (2013.01); *A61F 2002/30985* (2013.01); *A61F 2310/00023* (2013.01); *A61F 2310/00029* (2013.01); *A61F 2310/00059* (2013.01); *A61F 2310/00383* (2013.01); *B22F 3/1055* (2013.01); *B22F 3/11* (2013.01); *B22F 7/062* (2013.01); *B22F 7/08* (2013.01); *B22F 2207/17* (2013.01); *B22F 2998/10* (2013.01); *B22F 2999/00* (2013.01); *B33Y 10/00* (2014.12); *B33Y 80/00* (2014.12); *Y02P 10/295* (2015.11)

(58) Field of Classification Search
   CPC .... B22F 1/0018–0025; B22F 2007/047; B22F 2301/205; B22F 7/004; B23K 28/003
   USPC .................................................. 623/20.15
   See application file for complete search history.

(56) References Cited

U.S. PATENT DOCUMENTS

| | | | |
|---|---|---|---|
| 5,658,341 A | 8/1997 | Delfosse | |
| 5,672,284 A * | 9/1997 | Devanathan | A61F 2/30907 219/121.64 |
| 5,687,788 A | 11/1997 | Caldarise et al. | |
| 5,716,412 A | 2/1998 | DeCarlo, Jr. et al. | |
| 5,762,125 A | 6/1998 | Mastrorio | |
| 5,824,100 A | 10/1998 | Kester et al. | |
| 5,824,103 A | 10/1998 | Williams | |
| 5,897,592 A | 4/1999 | Caldarise et al. | |
| 5,910,173 A | 6/1999 | DeCarlo, Jr. et al. | |
| 5,980,974 A | 11/1999 | Armini et al. | |
| 6,087,553 A | 7/2000 | Cohen et al. | |
| 6,105,235 A | 8/2000 | Caldarise | |
| 6,165,221 A | 12/2000 | Schmotzer | |
| RE37,277 E | 7/2001 | Baldwin et al. | |
| 6,258,127 B1 | 7/2001 | Schmotzer | |
| 6,506,216 B1 | 1/2003 | McCue et al. | |
| 6,652,588 B2 | 11/2003 | Hayes, Jr. et al. | |
| 6,858,032 B2 | 2/2005 | Chow et al. | |
| 6,945,448 B2 | 9/2005 | Medlin et al. | |
| 6,974,625 B2 | 12/2005 | Hunter et al. | |
| 7,001,672 B2 | 2/2006 | Justin et al. | |
| 7,081,137 B1 | 7/2006 | Servidio | |
| 7,087,200 B2 | 8/2006 | Taboas et al. | |
| 7,105,030 B2 | 9/2006 | Despres, III et al. | |
| 7,160,330 B2 | 1/2007 | Axelson, Jr. et al. | |
| 7,182,786 B2 | 2/2007 | Justin et al. | |
| 7,189,262 B2 | 3/2007 | Hayes, Jr. et al. | |
| 7,258,810 B2 | 8/2007 | Hunter et al. | |
| 7,294,149 B2 | 11/2007 | Hozack et al. | |
| 7,309,339 B2 | 12/2007 | Cusick et al. | |
| 7,357,817 B2 | 4/2008 | D'Alessio, II | |
| 7,413,577 B1 | 8/2008 | Servidio | |
| 7,445,640 B2 | 11/2008 | Despres, III et al. | |
| 7,497,874 B1 | 3/2009 | Metzger et al. | |
| 7,513,912 B2 | 4/2009 | Hayes, Jr. et al. | |
| 7,524,334 B2 | 4/2009 | Haidukewych | |
| 7,537,664 B2 | 5/2009 | O'Neil et al. | |
| 7,578,851 B2 | 8/2009 | Dong et al. | |
| 7,625,407 B2 | 12/2009 | Akizuki et al. | |
| 7,628,817 B1 | 12/2009 | Axelson, Jr. et al. | |
| 7,632,575 B2 | 12/2009 | Justin et al. | |
| 7,648,735 B2 | 1/2010 | Hunter et al. | |
| 7,666,522 B2 | 2/2010 | Justin et al. | |
| 7,771,484 B2 | 8/2010 | Campbell | |
| 7,837,690 B2 | 11/2010 | Metzger | |
| 7,850,862 B2 | 12/2010 | Amrich et al. | |
| 7,857,858 B2 | 12/2010 | Justin et al. | |
| 7,887,542 B2 | 2/2011 | Metzger et al. | |
| 7,918,382 B2 * | 4/2011 | Charlebois | A61F 2/30767 228/248.1 |
| 7,938,833 B2 | 5/2011 | Bastian | |
| 8,070,821 B2 | 12/2011 | Roger | |
| 8,075,628 B2 | 12/2011 | Justin et al. | |
| 8,142,886 B2 | 3/2012 | Noble et al. | |
| 8,147,861 B2 | 4/2012 | Jones et al. | |
| 8,162,949 B2 | 4/2012 | Duggineni et al. | |
| 8,167,954 B2 | 5/2012 | Despres, III et al. | |
| 8,191,760 B2 | 6/2012 | Charlebois et al. | |
| 8,241,367 B2 | 8/2012 | Justin et al. | |
| 8,268,099 B2 | 9/2012 | O'Neill et al. | |
| 8,268,100 B2 | 9/2012 | O'Neill et al. | |
| 8,350,186 B2 | 1/2013 | Jones et al. | |
| 8,357,201 B2 | 1/2013 | Mayer et al. | |
| 8,388,887 B2 | 3/2013 | Gupta et al. | |
| 8,414,908 B2 | 4/2013 | Jin et al. | |
| 8,518,047 B2 | 8/2013 | Metzger et al. | |
| 8,551,100 B2 | 10/2013 | Metzger | |
| 8,556,981 B2 | 10/2013 | Jones et al. | |
| 8,632,600 B2 | 1/2014 | Zannis et al. | |
| 8,663,337 B2 | 3/2014 | Anderson et al. | |
| 8,715,359 B2 | 5/2014 | Deffenbaugh et al. | |
| 8,728,387 B2 | 5/2014 | Jones et al. | |
| 8,735,773 B2 | 5/2014 | Lang | |
| 8,758,444 B2 | 6/2014 | Wentorf et al. | |
| 8,790,345 B2 | 7/2014 | Anderson | |
| 8,843,229 B2 | 9/2014 | Vanasse et al. | |
| 8,870,883 B2 | 10/2014 | Metzger et al. | |
| 8,900,316 B2 | 12/2014 | Lenz et al. | |
| 8,900,317 B2 | 12/2014 | Zubok et al. | |
| 8,951,465 B2 | 2/2015 | Gupta | |
| 8,985,430 B2 | 3/2015 | Charlebois et al. | |
| 8,992,703 B2 | 3/2015 | O'Neill et al. | |
| 9,023,053 B2 | 5/2015 | Metzger | |
| 9,072,605 B2 | 7/2015 | Coon et al. | |
| 9,161,761 B2 | 10/2015 | Metzger et al. | |
| 9,192,459 B2 | 11/2015 | Bonutti | |
| 9,226,827 B2 | 1/2016 | Luscher | |
| 9,237,950 B2 | 1/2016 | Hensley et al. | |
| 9,265,613 B2 | 2/2016 | Nevins et al. | |
| 9,278,003 B2 | 3/2016 | Deffenbaugh et al. | |
| 9,289,301 B2 | 3/2016 | Mayer et al. | |
| 9,301,846 B2 | 4/2016 | Landon | |
| 9,370,605 B2 | 6/2016 | Zhang et al. | |
| 9,381,085 B2 | 7/2016 | Axelson, Jr. et al. | |
| 9,427,334 B2 | 8/2016 | Axelson, Jr. et al. | |
| 9,445,823 B2 | 9/2016 | Harris et al. | |

(56) References Cited

U.S. PATENT DOCUMENTS

| | | |
|---|---|---|
| 9,445,902 B2 | 9/2016 | Klein et al. |
| 9,445,909 B2 | 9/2016 | Cohen et al. |
| 9,452,051 B2 | 9/2016 | Collazo et al. |
| 9,456,901 B2 | 10/2016 | Jones et al. |
| 9,480,511 B2 | 11/2016 | Butters et al. |
| 9,517,134 B2 | 12/2016 | Lang |
| 9,517,138 B2 | 12/2016 | Zubok et al. |
| 9,554,862 B2 | 1/2017 | Davignon et al. |
| 9,636,229 B2 | 5/2017 | Lang et al. |
| 9,649,195 B2 | 5/2017 | Bechtold et al. |
| 9,655,632 B2 | 5/2017 | Dmuschewsky et al. |
| 9,656,358 B2 | 5/2017 | Charlebois et al. |
| 9,662,214 B2 | 5/2017 | Li et al. |
| 9,668,863 B2 | 6/2017 | Sharp et al. |
| 9,668,871 B2 | 6/2017 | Irwin et al. |
| 2006/0229715 A1* | 10/2006 | Istephanous .......... A61F 2/0077 623/1.46 |
| 2010/0016987 A1 | 1/2010 | Scrafton et al. |
| 2013/0218288 A1 | 8/2013 | Fonte et al. |
| 2014/0010951 A1 | 1/2014 | Vargas et al. |
| 2014/0257504 A1 | 9/2014 | Dong et al. |
| 2014/0257507 A1 | 9/2014 | Wang et al. |
| 2014/0316528 A1 | 10/2014 | Bechtold et al. |
| 2014/0371863 A1 | 12/2014 | Vanasse et al. |
| 2015/0032218 A1 | 1/2015 | Landon |
| 2015/0093283 A1 | 4/2015 | Miller et al. |
| 2015/0305754 A1 | 10/2015 | Metzger |
| 2015/0305878 A1 | 10/2015 | O'Neil et al. |
| 2015/0359638 A1 | 12/2015 | Khowaylo et al. |
| 2016/0157906 A1 | 6/2016 | Hollis et al. |
| 2016/0157908 A1 | 6/2016 | Cawley et al. |
| 2016/0199193 A1 | 7/2016 | Willis et al. |
| 2016/0213821 A1 | 7/2016 | Melkent et al. |
| 2016/0228255 A1 | 8/2016 | Samuelson et al. |
| 2016/0278929 A1 | 9/2016 | Harris et al. |
| 2016/0296289 A1 | 10/2016 | Choudhury et al. |
| 2016/0310279 A1 | 10/2016 | Samuelson et al. |
| 2016/0310282 A1 | 10/2016 | Bojarski et al. |
| 2016/0374814 A1 | 12/2016 | Collazo et al. |
| 2017/0027700 A1 | 2/2017 | Cohen et al. |
| 2017/0042576 A1 | 2/2017 | Butters et al. |
| 2017/0056025 A1 | 3/2017 | Trachsler et al. |
| 2017/0071744 A1 | 3/2017 | Bali et al. |
| 2018/0065324 A1* | 3/2018 | Isobe ....................... B22F 1/00 |

FOREIGN PATENT DOCUMENTS

| | | |
|---|---|---|
| AU | 2006252296 B2 | 7/2007 |
| AU | 2009212243 B2 | 8/2009 |
| AU | 2009270566 B2 | 1/2017 |
| CA | 2448592 C | 5/2004 |
| CA | 2859970 A1 | 7/2013 |
| CA | 2844788 C | 9/2014 |
| CN | 101732761 A | 6/2010 |
| EP | 1418013 B1 | 1/2005 |
| EP | 1683593 A2 | 7/2006 |
| EP | 1911468 B1 | 9/2009 |
| EP | 2210623 A1 | 7/2010 |
| EP | 1800700 B1 | 9/2010 |
| EP | 1398045 B1 | 6/2012 |
| EP | 2467097 A1 | 6/2012 |
| EP | 2709564 A1 | 3/2014 |
| EP | 2797557 A1 | 11/2014 |
| EP | 2797558 A1 | 11/2014 |
| EP | 2485778 B1 | 8/2015 |
| EP | 2685938 B1 | 8/2015 |
| EP | 2774580 B1 | 10/2016 |
| EP | 2967885 B1 | 12/2016 |
| EP | 2651341 B1 | 1/2017 |
| EP | 2874570 B1 | 1/2017 |
| EP | 3127510 A1 | 2/2017 |
| EP | 1803513 B1 | 3/2017 |
| EP | 2949293 B1 | 3/2017 |
| EP | 3178448 A1 | 6/2017 |
| GB | 2388034 B | 11/2013 |
| WO | 2012021764 A2 | 2/2012 |
| WO | WO2016010895 A1 | 1/2016 |

OTHER PUBLICATIONS

Size Controlled Mechochemical Synthesis of ZrSi2, David Restrepo, Aug. 30, 2012.

Bone Ingrowth Performance of OsteoSync Ti, Document: 2007-001-40 REV A.

Mechanical Characteristics of OsteoSync Ti, Document: 2007-001-41 REV A.

International Search Report and Written Opinion for corresponding International Application No. PCT/US2018/019647 dated Jun. 14, 2018.

* cited by examiner

COMPOSITE JOINT ARTHROPLASTY SYSTEMS AND METHODS

TECHNICAL FIELD

The present disclosure relates to surgical systems and methods. More specifically, the present disclosure relates to implants and related methods for joint arthroplasty.

BACKGROUND

Joint arthroplasty procedures are surgical procedures in which one or more articulating surfaces of a joint are replaced with prosthetic articulating surfaces. Such procedures are becoming increasingly commonplace, for many joints of the body.

For a successful joint arthroplasty, it is important that the implants remain in place and maintain the necessary wear characteristics. Further, it is desirable for the arthroplasty procedure to be carried out quickly and smoothly. Many existing joint arthroplasty implants and methods are time-consuming to implant, do not form a sufficient attachment to the underlying bone, or leave excessive wear debris.

SUMMARY

The various systems and methods of the present disclosure have been developed in response to the present state of the art, and in particular, in response to the problems and needs in the art that have not yet been fully solved by currently available joint arthroplasty systems and methods. The systems and methods of the present disclosure may provide joint implants and instruments that provide enhanced bone fixation, less wear debris, and/or streamlined implantation.

According to some embodiments, a prosthesis may be designed to replace an articular surface on bone. The prosthesis may have an articulating component formed via casting, and a bone anchoring component having a 3D printed structure. The articulating component may have an articulating component joint-facing side with an articular surface, and an articulating component bone-facing side with a bone-facing shape. The bone anchoring component may have a bone anchoring component joint-facing side with a joint-facing shape that is complementary to the bone-facing shape, and a bone anchoring component bone-facing side. The bone anchoring component joint-facing side may be secured to the articulating component bone-facing side. The bone anchoring component bone-facing side may have a bone engagement surface having a porous structure with pores selected to facilitate in-growth of the bone into the pores.

The bone anchoring component may be formed of DMLS (direct metal laser sintered) Titanium, and the 3D printed structure may have a porous structure. The porous structure may have a lower porosity on the bone anchoring component joint-facing side than on the bone anchoring component bone-facing side. The bone anchoring component joint-facing side may have a near solid structure with little or no porosity.

The bone anchoring component bone-facing side may have a surface layer of Titanium Dioxide nanotubes formed via anodization. The Titanium Dioxide nanotubes may have an anatase structure.

The articulating component may be formed of an alloy of Cobalt Chromium. The alloy of Cobalt Chromium may have one or more crystalline structures established by a casting process used to form the articulating component. The bone anchoring component joint-facing side may be secured to the articulating component bone-facing side via a bonding process occurring at a bonding temperature far below melting temperatures of Cobalt and Chromium, such the crystalline structures are not significantly modified by the bonding process. The bonding process may occur at a bonding temperature of about 500° C. The prosthesis may further have a bonding zone, between the bone anchoring component joint-facing side and the articulating component bone-facing side, formed of melted and re-solidified Titanium nanoparticles.

The bone anchoring component joint-facing side may additionally or alternatively be secured to the articulating component bone-facing side via a laser welding process around the perimeter and/or along the seams of the two components. Additionally or alternatively, the two components may also be laser welded along the perimeter and/or seams with the addition of a metallic powder and binder mixture along the weld lines. Specifically, a metal powder and binder mixture may be placed along the weld lines and subsequently melted with a laser. The re-solidified metal may bond the bone anchoring component and the articulating component together. The metallic powder and binder mixture may include titanium powder and a binder consisting of gelatin, glycerin and/or PVA. The metallic powder may additionally or alternatively include a cobalt and chromium powder and a binder consisting of gelatin, glycerin or PVA.

According to some embodiments, a method may be designed for manufacturing a prosthesis for replacing an articular surface on a bone. The method may include casting an articulating component with an articulating component joint-facing side with an articular surface, and an articulating component bone-facing side with a bone-facing shape. The method may further include 3D printing a bone anchoring component with a bone anchoring component joint-facing side with a joint-facing shape that is complementary to the bone-facing shape, and a bone anchoring component bone-facing side with a bone engagement surface having a porous structure with pores selected to facilitate in-growth of the bone into the pores. The method may further include securing the bone anchoring component joint-facing side to the articulating component bone-facing side.

3D printing the bone anchoring component may include direct metal laser sintering Titanium to form a porous structure. Forming the porous structure may include providing lower porosity on the bone anchoring component joint-facing side than on the bone anchoring component bone-facing side.

The method may further include anodizing the bone anchoring component to form a surface layer of Titanium Dioxide nanotubes on the bone anchoring component joint-facing side. The method may further include heating the bone anchoring component to a temperature sufficient to change at least a portion of the surface layer of Titanium Dioxide nanotubes to anatase.

Casting the articulating component may include casting the articulating component from an alloy of Cobalt Chromium. Casting the articulating component may include establishing one or more crystalline structures of the alloy of Cobalt Chromium. Securing the bone anchoring component joint-facing side to the articulating component bone-facing side may include heating at least the bone anchoring component joint-facing side and the articulating component bone-facing side to a bonding temperature far below melting temperatures of Cobalt and Chromium, so as to avoid significantly modifying the crystalline structures. The method may further include, prior to heating at least the bone anchoring component joint-facing side and the articulating component bone-facing side to the bonding temperature, applying a paste to one or both of the bone anchoring component joint-facing side and the articulating component bone-facing side. The paste may include a gelatin and/or glycerin and Titanium nanoparticles.

The method may further include, after applying the paste on one or both of the bone anchoring component joint-facing side and the articulating component bone-facing side, and prior to heating at least the bone anchoring component joint-facing side and the articulating component bone-facing side to the bonding temperature, assembling the articulating component and the bone anchoring component such that the paste is sandwiched between the bone anchoring component joint-facing side and the articulating component bone-facing side, and pressing the bone anchoring component joint-facing side and the articulating component bone-facing side together. Heating at least the bone anchoring component joint-facing side and the articulating component bone-facing side to the bonding temperature may include, with the bone anchoring component joint-facing side and the articulating component bone-facing side pressed together, heating at least the bone anchoring component joint-facing side and the articulating component bone-facing side in a two-step heating process to about 500° C. to debind the gelatin/glycerin from the paste and melt the Titanium nanoparticles. The debinding process may be at a temperature below 500° C. and after the gelatin/glycerin is sufficiently removed by debinding, the components may then be heated to about 500° C. for Titanium nanoparticle melting.

In other attachment methods, a laser process may be used to melt the metal of the bone anchoring component and the articulating component along the perimeter and/or along the seams. Additionally or alternatively, a metal powder and binder mixture may be placed along the parameter and seams between the bone anchoring and articulating components and subsequently melted with a laser. The re-solidified metal powder may bond the bone anchoring component and the articulating component together.

Further, according to some embodiments, a method may be designed to manufacture a prosthesis for replacing an articular surface on a bone. The method may include casting metals comprising at least Cobalt and Chromium to form an articulating component with an articulating component joint-facing side with an articular surface, and an articulating component bone-facing side with a bone-facing shape. The method may further include direct metal laser sintering Titanium to form a bone anchoring component with a bone anchoring component joint-facing side with a joint-facing shape that is complementary to the bone-facing shape, and a bone anchoring component bone-facing side with a bone engagement surface having a porous structure with pores selected to facilitate in-growth of the bone into the pores. The method may further include applying a paste containing Titanium nanoparticles to at least one of the bone anchoring component joint-facing side and the articulating component bone-facing side, assembling the articulating component and the bone anchoring component such that the paste is sandwiched between the bone anchoring component joint-facing side and the articulating component bone-facing side, and heating the paste to a bonding temperature sufficient to commence melting of the Titanium nanoparticles to secure the bone anchoring component joint-facing side to the articulating component bone-facing side.

The method may further include anodizing the bone anchoring component to form a surface layer of Titanium Dioxide nanotubes on the bone anchoring component joint-facing side, and, after assembling the articulating component and the bone anchoring component, pressing the articulating component and the bone anchoring component together. The paste may further include gelatin and/or glycerin. Heating the paste to the bonding temperature may include, with the articulating component and the bone anchoring component pressed together, heating at least the bone anchoring component joint-facing side and the articulating component to a temperature below 500° C. to debind the gelatin/glycerin, and then heating the bone anchoring component joint-facing side to about 500° C. to melt the Titanium nanoparticles, and changing at least a portion of the surface layer of Titanium Dioxide nanotubes to anatase.

These and other features and advantages of the present disclosure will become more fully apparent from the following description and appended claims, or may be learned by the practice of the systems and methods set forth hereinafter.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the scope of the appended claims, the exemplary embodiments of the present disclosure will be described with additional specificity and detail through use of the accompanying drawings in which:

DETAILED DESCRIPTION

Exemplary embodiments of the disclosure will be best understood by reference to the drawings, wherein like parts are designated by like numerals throughout. It will be readily understood that the components of the disclosure, as generally described and illustrated in the Figures herein, could be arranged and designed in a wide variety of different configurations. Thus, the following more detailed description of the embodiments of the apparatus, system, and method, as represented in FIGS. 1 through 5, is not intended to limit the scope of the claims, as claimed, but is merely representative exemplary of exemplary embodiments.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

The systems and methods of the present disclosure may be used in connection with a wide variety of implant types. The systems and methods disclosed herein may have particular applicability to implants that benefit from having disparate materials, such as porous materials for bone engagement and hard or nonporous materials for articulation. Thus, the systems and methods set forth herein may be of particular benefit for joint replacement implants. This disclosure focuses on knee arthroplasty implants; however, those of skill in the art will recognize that it may readily be applied to other joint arthroplasty implants, or to implants designed for other purposes besides joint arthroplasty.

Figure 1:
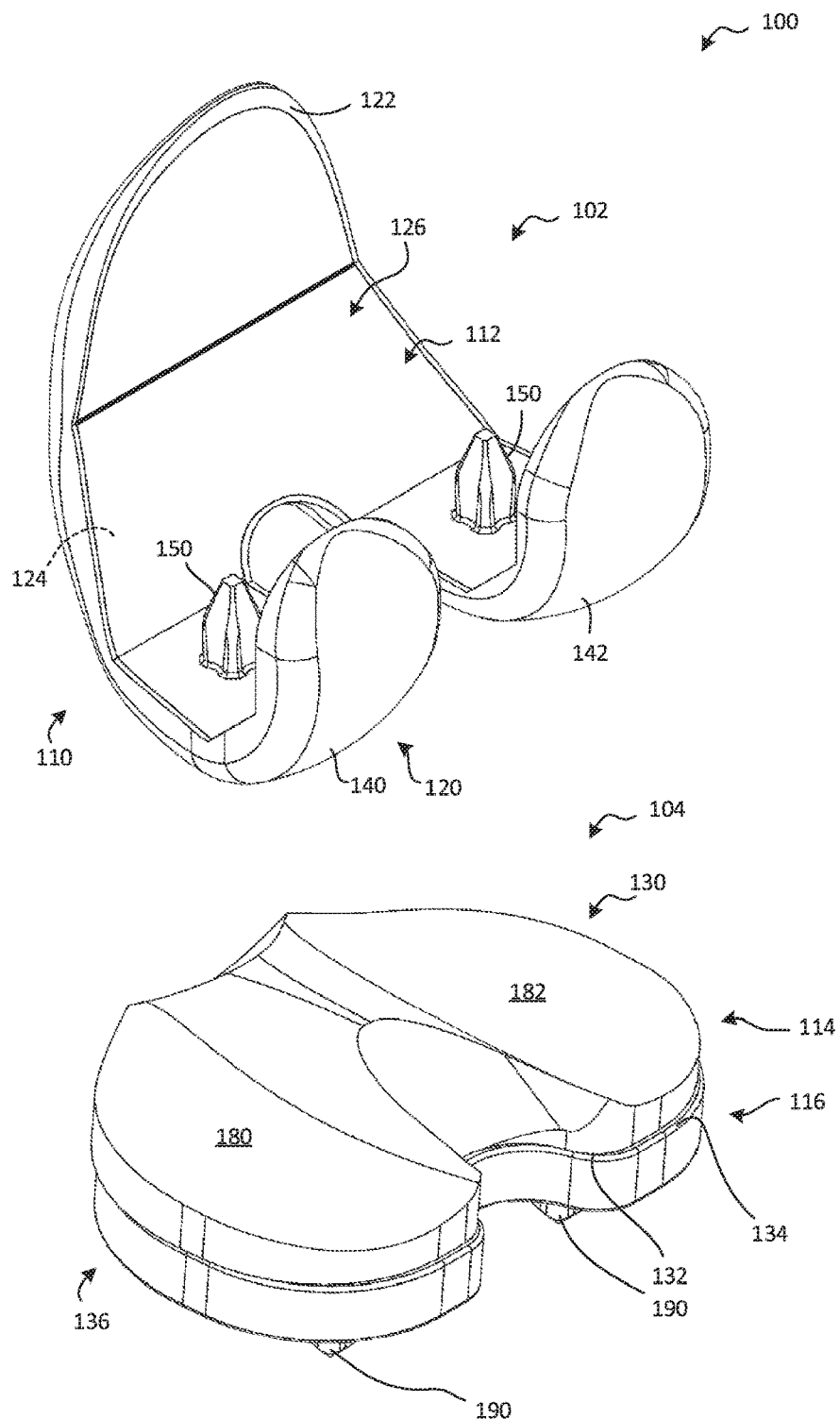
FIG. 1 is a perspective view of a knee arthroplasty system according to one embodiment.

FIG. 1 is a perspective view of a knee arthroplasty system, or system 100, according to one embodiment. The system 100 may be designed to replace the natural articulating surfaces of a knee joint, and may thus have a femoral prosthesis 102 and a tibial prosthesis 104. In some embodiments, the system 100 may be designed to replace only the femoral or tibial articulating surfaces, and may thus include only the femoral prosthesis 102 or the tibial prosthesis 104.

The femoral prosthesis 102 and the tibial prosthesis 104 may each have an articulating component with replacement articulating surfaces, and a bone anchoring component secured to the articulating component to secure the articulating component to the underlying bone. Specifically, the femoral prosthesis 102 may have a femoral articulating component 110 and a femoral bone anchoring component 112. Similarly, the tibial prosthesis 104 may have a tibial articulating component 114 and a tibial bone anchoring component 116.

Each of the aforementioned articulating components and bone anchoring components may have a joint-facing side and a bone-facing side. Thus, the femoral articulating component 110 may have a joint-facing side 120 and a bone-facing side 122, and the femoral bone anchoring component 112 may have a joint-facing side 124 and a bone-facing side 126. Similarly, the tibial articulating component 114 may have a joint-facing side 130 and a bone-facing side 132, and the tibial bone anchoring component 116 may have a joint-facing side 134 and a bone-facing side 136.

The bone-facing side 122 of the femoral articulating component 110 may have a shape that matches the shape of the joint-facing side 124 of the femoral bone anchoring component 112, and may be secured to the joint-facing side 124 of the femoral bone anchoring component 112 in a manner that will be set forth in greater detail subsequently. Similarly, the bone-facing side 132 of the tibial articulating component 114 may have a shape that matches the shape of the joint-facing side 134 of the tibial bone anchoring component 116, and may be secured to the joint-facing side 134 of the tibial bone anchoring component 116 in a manner that will be set forth in greater detail subsequently.

The joint-facing side 120 of the femoral articulating component 110 may have a first articulating surface 140 and a second articulating surface 142, which are shaped to mimic the shapes of the natural articulating surfaces on the end of the femur. The shapes depicted in FIG. 1 are merely exemplary; according to alternative embodiments, any articulating surface shape known in the art may be used.

The bone-facing side 126 of the femoral bone anchoring component 112 may have one or more features that enhance engagement of the femoral bone anchoring component 112 with the underlying bone. For example, the bone-facing side 126 of the femoral bone anchoring component 112 may have a pair of posts 150 that protrude from the bone-facing side 126 of the femoral bone anchoring component 112. Optionally, other bone anchoring features (not shown), as known in the art, may be used in addition to or in the alternative to the posts 150.

The joint-facing side 130 of the tibial articulating component 114 may also have a first articulating surface 180 and a second articulating surface 182. After implantation of the femoral prosthesis 102 and the tibial prosthesis 104, the first articulating surface 140 may articulate with the first articulating surface 180, and the second articulating surface 142 may articulate with the second articulating surface 182. The articulation of the femoral articulating component 110 with the tibial articulating component 114 may be designed to mimic that of the natural knee joint.

The bone-facing side 136 of the tibial bone anchoring component 116 may have a plurality of posts 190 that protrude into the bone from the remainder of the bone-facing side 136. Optionally, other bone anchoring features (not shown), as known in the art, may be used in addition to or in the alternative to the posts 190.

Figure 2:
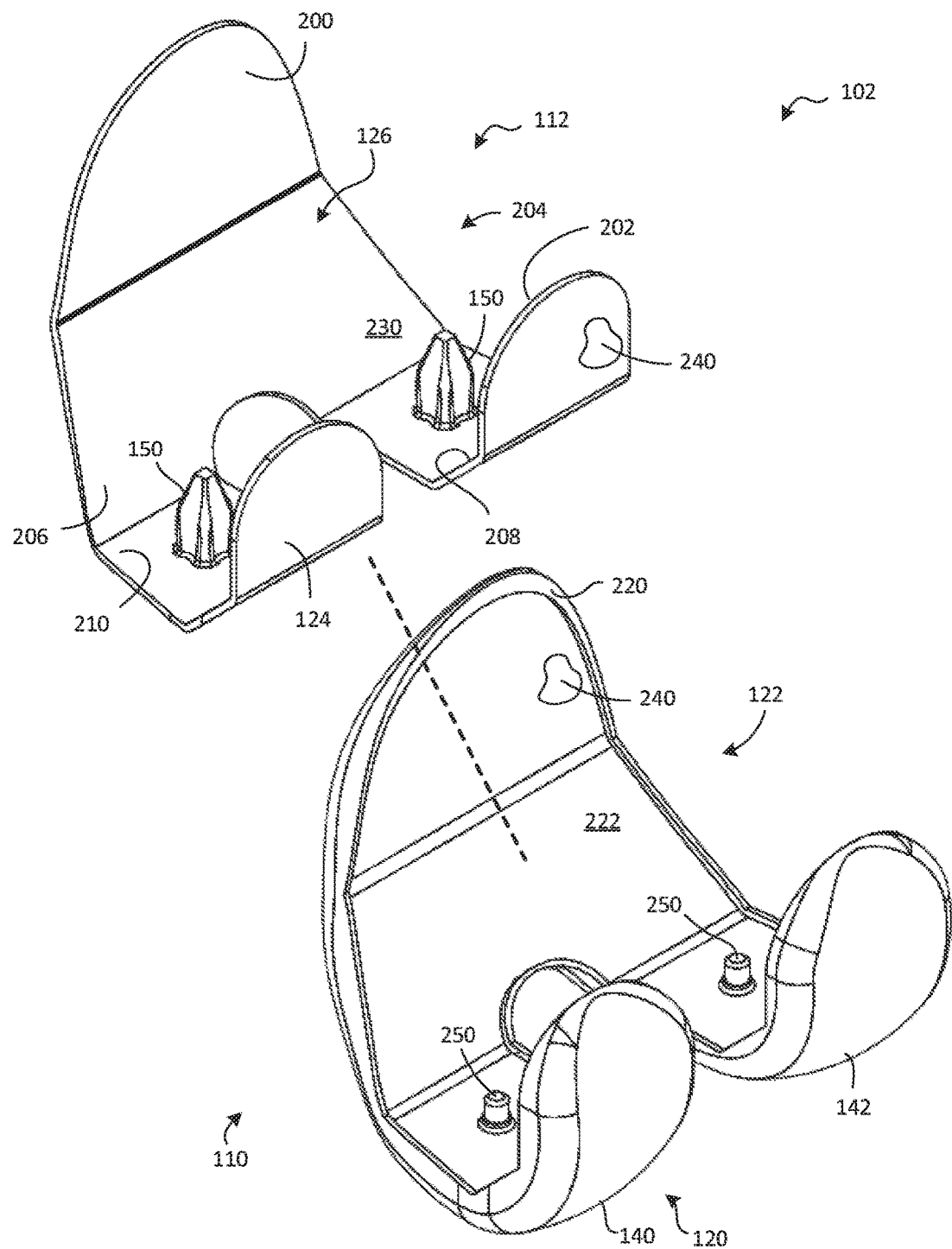
FIG. 2 is an exploded, perspective view of the femoral prosthesis of the knee arthroplasty system of FIG. 1.

FIG. 2 is an exploded, perspective view of the femoral prosthesis 102 of the system 100 of FIG. 1. The femoral articulating component 110 and the femoral bone anchoring component 112 may optionally be manufactured separately from each other. Accordingly, different manufacturing processes may be used to form the femoral articulating component 110 and the femoral bone anchoring component 112. This may advantageously enable the use of materials and/or processes for each of the femoral articulating component 110 and the femoral bone anchoring component 112 that are best suited for the role to be performed.

For example, the femoral articulating component 110 may be designed to endure cyclical loading in friction and compression. Accordingly, high-strength and/or low-wear materials and surface properties may be desired. Accordingly, the femoral articulating component 110 may be made of a relatively hard material such as an alloy of Cobalt Chromium ("Cobalt Chrome,"). Specifically, the femoral articulating component 110 may be made of an alloy of Cobalt Chromium Molybdenum (CoCrMo). A manufacturing process such as casting may be used. In some embodiments, the first articulating surface 140 and the second articulating surface 142 may be specially processed in a manner that increases their hardness and/or wear resistance.

Conversely, the femoral bone anchoring component 112 may be designed to provide high-strength fixation of the femoral articulating component 110 to the underlying bone. It may be desirable for the femoral bone anchoring component 112 to have a porous structure that encourages bone in-growth. Accordingly, the femoral bone anchoring component 112 may be formed of a metal such as Titanium, or specifically, direct metal laser sintered ("DMLS") Titanium. The femoral bone anchoring component 112 may be formed via an additive manufacturing method such as 3D printing. Such manufacturing methods may facilitate the creation of a porous structure, particularly on the bone-facing side 126 of the femoral bone anchoring component 112.

In some embodiments, the femoral bone anchoring component 112 may be made such that the porosity varies in a gradient through the thickness of the femoral bone anchoring component 112. Thus, the bone-facing side 126 of the femoral bone anchoring component 112 may be made more porous to facilitate bone in-growth, while the joint-facing side 124 of the femoral bone anchoring component 112 may be made less porous to enhance attachment of the joint-facing side 124 to the bone-facing side 122 of the femoral articulating component 110. In some embodiments, the joint-facing side 124 may be made substantially solid (i.e., nonporous) to enhance adhesion to the bone-facing side 122 of the femoral articulating component 110, while the bone-facing side 126 may be highly porous.

As shown, the bone-facing side 122 of the femoral articulating component 110 may have an anterior portion 200, a posterior portion 202, and a distal portion 204. Upon implantation of the femoral articulating component 110, the anterior portion 200 may be located on the anterior side of the knee, the posterior portion 202 may be located on the posterior side of the knee, and the distal portion 204 may be located at the distal end of the femur. The distal portion 204 may be divided into three faces: an anterior-distal face 206, a posterior-distal face 208, and a distal face 210. The anterior-distal face 206 may reside between the anterior portion 200 and the distal face 210, and the posterior-distal face 208 may be reside between the posterior portion 202 and the distal face 210. As shown, the posts 150 may protrude from the distal face 210.

The posts 150 may all protrude in a cephalad direction so that these features can penetrate the bone, helping to anchor the femoral articulating component 110 on the distal end of the femur (not shown). The posts 150 may optionally be shaped to facilitate entry into and/or compaction of the bone. Thus, the bone surrounding the posts 150 in their implanted state may be compacted and/or strengthened.

As also shown in FIG. 2, the bone-facing side 122 of the femoral articulating component 110 may have a peripheral ridge 220 that defines an interior recess 222. The shape of the interior recess 222 may closely match that of the joint-facing side 124 of the femoral bone anchoring component 112 so that the joint-facing side 124 of the femoral bone anchoring component 112 can be secured to the interior recess 222. When the femoral bone anchoring component 112 and the femoral articulating component 110 are assembled together, the bone-facing side 126 of the femoral bone anchoring component 112 may lie substantially flush with the peripheral ridge 220 of the bone-facing side 122 of the femoral articulating component 110.

In some embodiments, the bone-facing side 126 of the femoral bone anchoring component 112 may be treated to enhance porosity and/or bone in-growth. In some examples, the bone-facing side 126 of the femoral bone anchoring component 112 may be processed via a process such as anodizing to form Titanium Dioxide nanotubes on the bone-facing side 126. Specifically, the bone-facing side 126 may be anodized in a Fluoride electrolyte, as set forth in U.S. application Ser. No. 11/913,062, filed Jun. 10, 2008 and entitled "Compositions Comprising Nanostructures for Cell, Tissue and Artificial Organ Growth, and Methods for Making and Using Same, now U.S. Pat. No. 8,414,908, which is incorporated by reference as though set forth herein in its entirety. The result may be the formation of a surface layer 230 of Titanium Dioxide nanotubes on the bone-facing side 126.

The femoral articulating component 110 and the femoral bone anchoring component 112 may be secured together in a variety of ways. One exemplary attachment method will be set forth as follows. Those of skill in the art will recognize that various steps set forth below may be omitted, replaced with alternative steps, and/or supplemented with additional steps not specifically provided herein. Further, the following steps are not limited to knee implants, but may be used in connection with any implant having an articulating component and a bone engagement component.

A paste 240 may be made from nanoparticles of a metal such as commercially pure Titanium. The nanoparticles may be formed in a variety of ways. According to one embodiment, Titanium nanoparticles may be made by ball milling a Titanium halide such as Titanium Chloride, with a metal reactant such as Magnesium. However, other metals, such as those of group 1 and group 2, may be used for the reactant. The mechanical action and formation of salt byproduct may prevent particle growth and produce fine particles. The salt byproduct may be removed via solvation in water or an aprotic solvent with a high dielectric constant, such as formaldehyde. Further details may be found in Blair, R. G., E. G. Gillan, N. K. B. Nguyen, D. Daurio, and R. B. Kaner, Rapid solid-state synthesis of titanium aluminides. Chemistry of Materials, 2003. 15(17): p. 3286-3293, and in Restrepo, D., S. M. Hick, C. Griebel, J. Alarcon, K. Giesler, Y. Chen, N. Orlovskaya, and R. G. Blair, Size controlled mechanochemical synthesis of $ZrSi_2$. Chemical Communications, 2013. 49: p. 707-709.

The result may be formation of nanoparticles of Titanium. The nanoparticles may be less than 20 nm in cross-sectional size, and need not be spherical but may instead be flake-shaped. The nanoparticles may thus have a melting temperature much lower than that of bulk Titanium. In order to provide a consistently lowered melting temperature, it may be desirable to provide the nanoparticles in a fairly tight Gaussian distribution, for example, 15 nm average size, +/−5 nm. Even a few particles greater than 25 nm in size may cause the melting temperature to rise. The low melting temperature may help the nanoparticles to melt into the adjoining material (for example, CrCo and Ti) and mechanically bond therewith, rather than diffusion bonding, as will be discussed subsequently.

The Titanium nanoparticles may be added to material such as a gelatin and/or glycerin to form the paste 240. The paste may be applied to one or both of the surfaces to be secured together, which, for the femoral prosthesis 102, may be the joint-facing side 124 of the femoral bone anchoring component 112 and the interior recess 222 of the bone-facing side 122 of the femoral articulating component 110. The paste 240 depicted in FIG. 2, on the joint-facing side 124 and the interior recess 222 is merely exemplary; it may be advantageous to spread the paste 240 over substantially the entire surface of the joint-facing side 124 or the interior recess 222.

The paste 240 may be applied in a variety of ways, such as spraying the surface to be coated, immersing the surface to be coated in a quantity of the paste, and/or spreading the paste 240 on the surface with a brush or other implement. The use of the gelatin and/or glycerin may facilitate adhesion of the paste 240 to the joint-facing side 124 and the bone-facing side 122.

The femoral articulating component 110 and the femoral bone anchoring component 112 may then be assembled together such that the joint-facing side 124 of the femoral bone anchoring component 112 is in contact with the bone-facing side 122 of the femoral articulating component 110. The femoral articulating component 110 and the femoral bone anchoring component 112 may be compressed together. In some embodiments, this may be done by positioning the femoral articulating component 110 above the femoral bone anchoring component 112, so that the weight of the femoral articulating component 110 urges the femoral articulating component 110 against the femoral bone anchoring component 112. Alternatively, a carbon fixture or other implement may be used to urge the femoral articulating component 110 and the femoral bone anchoring component 112 together.

The femoral articulating component 110 and the femoral bone anchoring component 112 may then be placed into a vacuum furnace or other heating implement. If desired, the femoral articulating component 110 and the femoral bone anchoring component 112 may continue to be compressed together as these parts are inserted into the furnace and heated. The furnace may then be used to heat the femoral articulating component 110 and the femoral bone anchoring component 112.

As the temperature of the femoral articulating component 110 and/or the femoral bone anchoring component 112 reaches about 200-300° C., the gelatin and/or glycerin may be burned away (debind process), and Carbon may be outgassed from the partial pressure vacuum furnace via an inert carrier gas. The Titanium nanoparticles may be left with air between their spheres. The furnace may be used to further heat the femoral articulating component 110 and the femoral bone anchoring component 112 to a bonding temperature of about 500° C., at which the Titanium nanoparticles may begin to melt, securing the joint-facing side 124 of the femoral bone anchoring component 112 to the bone-facing side 122 of the femoral articulating component 110. The femoral articulating component 110 and the femoral bone anchoring component 112 may then be removed from the furnace and allowed to cool.

At the bonding temperature, the Titanium Dioxide nanotubes may turn into anatase. This may be advantageous because, when compared with amorphous Titanium Dioxide, anatase may have greater strength and superior bone bonding characteristics. Thus, the surface properties of the bone-facing side 126 of the femoral bone anchoring component 112 may be enhanced by the process used to bond the femoral bone anchoring component 112 to the femoral articulating component 110.

Advantageously, the maximum temperature of this process may be the bonding temperature, which may be much lower than the melting temperatures of the significant constituent metals of which the femoral articulating component 110 is formed. Specifically, the melting temperature of Cobalt is 1,995° C., the melting temperature of Chromium is 1,907° C., and the melting temperature of Molybdenum is 2,623° C. Thus, the bonding process used to secure the femoral articulating component 110 to the femoral bone anchoring component 112 may not change the crystalline structure of the femoral bone anchoring component 112, as determined by the manufacturing process (for example, casting) used to form the femoral bone anchoring component 112. Thus, formation of brittle alloys may be avoided, which may occur in known processes in which conventional Titanium is diffusion bonded to Cobalt Chromium Molybdenum.

In addition to or in the alternative to the use of Titanium nanoparticles, a variety of other metals may be used to bond the femoral articulating component 110 to the femoral bone anchoring component 112. Nanoparticles of metals often have melting temperatures lower than those of the corresponding bulk metals; accordingly, a wide variety of nanoparticles, including Titanium, Cobalt, and Chromium nanoparticles, may be used. Additionally or alternatively, metals with lower melting temperatures than Titanium, Cobalt, and Chromium may be used in bulk, rather than nanoparticle, form. For example, Nitinol has a melting temperature of about 1400° C., which is also lower than the melting temperatures of Titanium, Cobalt, and Chromium. Thus, the paste 240, in some embodiments may include a Nitinol powder, which need not be in the form of nanoparticles.

The bond formed between the joint-facing side 124 of the femoral bone anchoring component 112 and the bone-facing side 122 of the femoral articulating component 110 may be a physical bond rather than a metallurgical bond. Thus, the Titanium nanoparticles may flow into surface irregularities in the joint-facing side 124 of the femoral bone anchoring component 112 and/or the bone-facing side 122 of the femoral articulating component 110 so that, when the Titanium nanoparticles re-freeze, they secure the femoral articulating component 110 and the femoral bone anchoring component 112 together. Avoidance of a metallurgical bond is advantageous in that such bonds can disrupt the crystalline structure of the materials being bonded. Thus, the low bonding temperature of the method set forth herein has many advantages, and may provide the femoral prosthesis 102 with enhanced wear resistance and/or bone adhesion.

A second attachment method may be used in addition to or in the alternative to the foregoing. The femoral bone anchoring component 112 may be placed in the interior recess 222 of the bone-facing side 122 of the femoral articulating component 110. A laser may be used to melt the metal of both components together along the perimeter and/or along the seams between the femoral bone anchoring component 112 and the femoral articulating component 110.

A third attachment method may be used in addition to or in the alternative to either or both of the foregoing. A metallic powder and binder mixture may be placed along the perimeter and/or the seams of the femoral bone anchoring component 112 prior to placement of the femoral bone anchoring component 112 in the interior recess 222 of the bone-facing side 122 of the femoral articulating component 110. A laser may be used to melt the metal powder and binder mixture along the perimeter and/or the seams. The re-solidified metal may bond the femoral bone anchoring component 112 and the femoral articulating component 110 together.

In addition to or in the alternative to the foregoing attachment methods, the methods disclosed in U.S. application Ser. No. 10/455,846, filed Jun. 6, 2003 and entitled "METHOD FOR ATTACHING A POROUS METAL LAYER TO A METAL SUBSTRATE," now U.S. Pat. No. 6,945,448, may be used. This application is incorporated as though set forth herein in its entirety.

The same method (or a similar method) may be used to secure the tibial articulating component 114 to the tibial bone anchoring component 116. Further, as mentioned previously, such bonding methods may be used not just for knee implants, but for other types of implants, and in particular, orthopedic implants in which an articulating component is to be secured to a bone anchoring component.

The method set forth above may be effective for relatively smooth surfaces. However, if desired, the surfaces to be bonded together may have features that facilitate and/or enhance the results of the bonding process. For example, the bone-facing side 122 of the femoral articulating component 110 may have features that cooperate with corresponding features (shown in FIG. 4) on the joint-facing side 124 of the femoral bone anchoring component 112 to help align the femoral articulating component 110 with the femoral bone anchoring component 112 and/or add mechanical fastening to the bonding described above. These features of the bone-facing side 122 may include, by way of example, a pair of post bosses 250.

Figure 3:
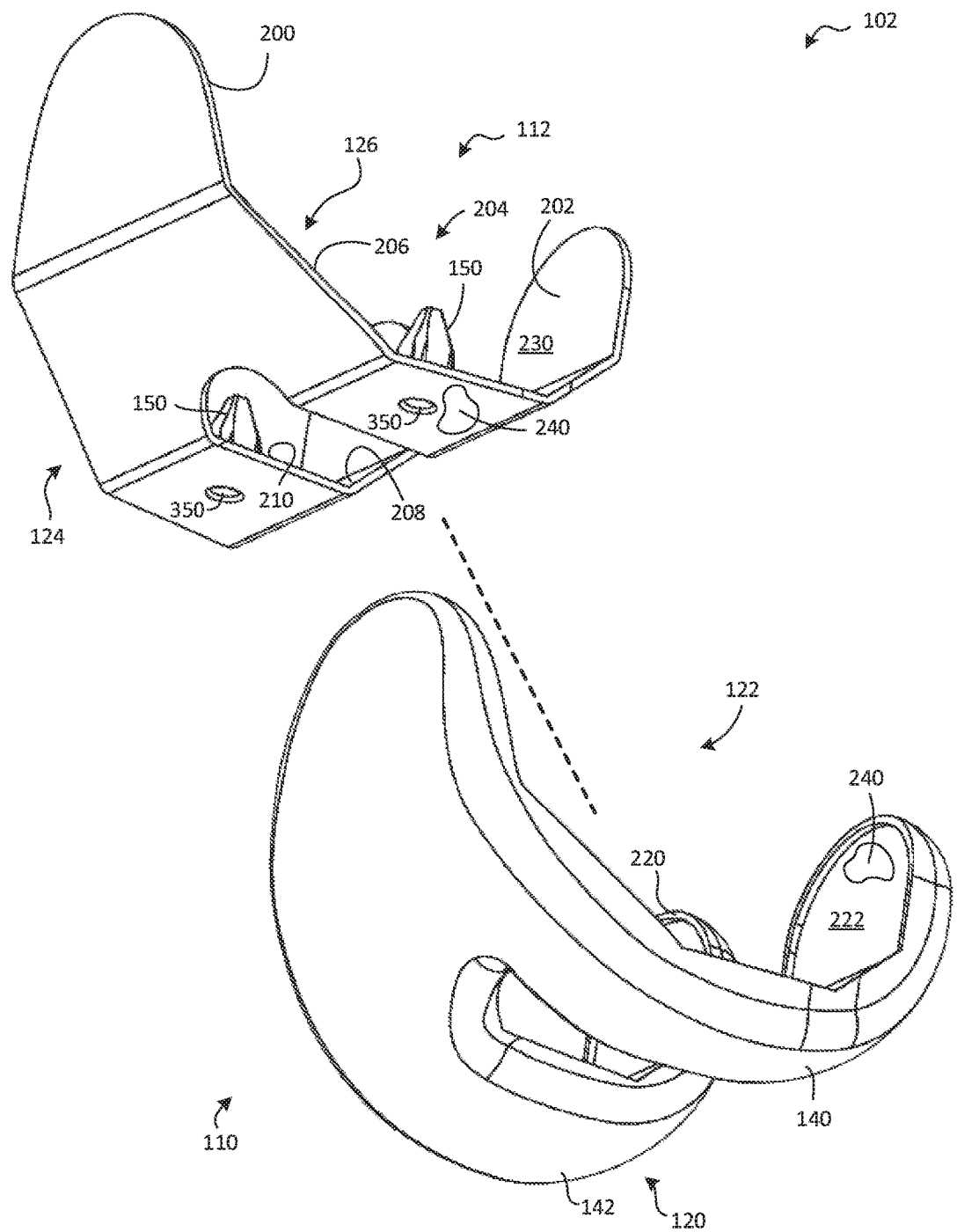
FIG. 3 is an exploded, perspective view, from a different viewpoint, of the femoral prosthesis of the knee arthroplasty system of FIG. 1.

FIG. 3 is an exploded, perspective view, from a different viewpoint, of the femoral prosthesis 102 of the system 100 of FIG. 1. The joint-facing side 124 of the femoral bone anchoring component 112 and the joint-facing side 120 of the femoral articulating component 110 are more clearly visible.

As shown, the joint-facing side 124 of the femoral bone anchoring component 112 may have features that cooperate with the post bosses 250 of the bone-facing side 122 of the femoral articulating component 110 depicted in FIG. 2. These features may include, for example, post bores 350. Each of the post bores 350 may reside in the interior of one of the posts 150. The post bores 350 may be shaped to receive the post bosses 250. If desired, the post bosses 250 may each be tapered to facilitate insertion into the post bores 350.

The features of the bone-facing side 122 may be received by these features of the joint-facing side 124 with some interference, which may cooperate with the bond described above to enhance attachment of the bone-facing side 122 to the joint-facing side 124. When the femoral articulating component 110 and the femoral bone anchoring component 112 are compressed together, as set forth above, the compression may be sufficient to urge the post bosses 250 into the post bores 350.

Additionally or alternatively, the heat applied to the femoral articulating component 110 and the femoral bone anchoring component 112 may cause thermal expansion eases insertion of the post bosses 250 into the post bores 350. The femoral articulating component 110 may be made such that the femoral articulating component 110 has higher thermal expansion than the femoral bone anchoring component 112. Thus, after insertion of the bosses into the bores, the femoral articulating component 110 and the femoral bone anchoring component 112 may be cooled, allowing the bores to tighten around the bosses.

In alternative embodiments, other positive and/or negative features may be used. Further, if desired, the positive features may be on the joint-facing side 124 of the femoral bone anchoring component 112, and the negative features may be on the bone-facing side 122 of the femoral articulating component 110.

Figure 4:
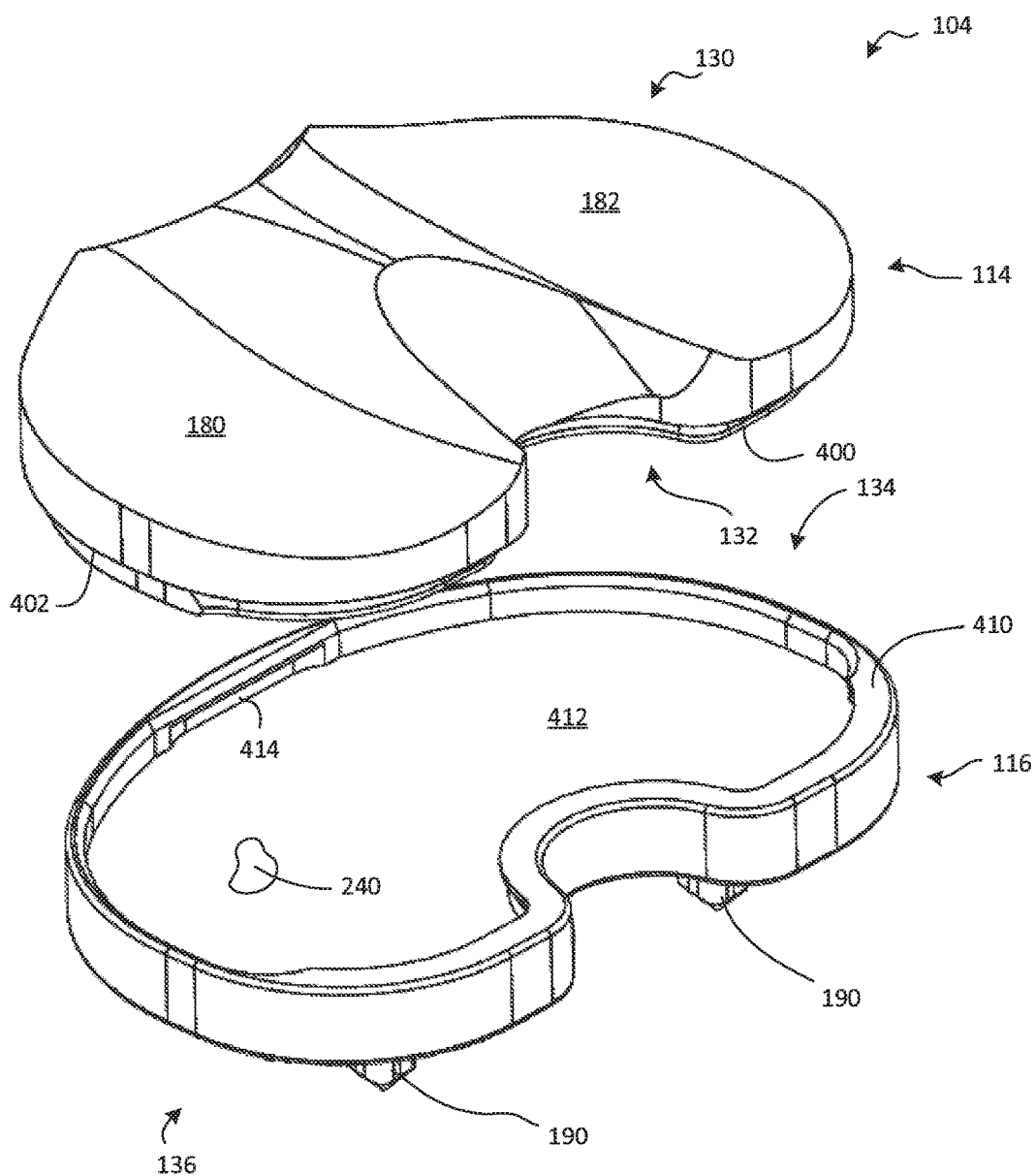
FIG. 4 is an exploded, perspective view of the tibial prosthesis of the knee arthroplasty system of FIG. 1.

FIG. 4 is an exploded, perspective view of the tibial prosthesis 104 of the system 100 of FIG. 1. As with the femoral prosthesis 102, the tibial articulating component 114 and the tibial bone anchoring component 116 may optionally be manufactured separately from each other. Accordingly, different manufacturing processes may be used to form the tibial articulating component 114 and the tibial bone anchoring component 116. For example, the tibial articulating component 114 may be formed via casting, and the tibial bone anchoring component 116 may be formed via additive manufacturing such as 3D printing.

Like the femoral articulating component 110, the tibial articulating component 114 may be made of Cobalt Chromium, or Cobalt Chromium Molybdenum. Similarly, like the femoral bone anchoring component 112, the tibial bone anchoring component 116 may be made of DMLS Titanium. A gradient of porosities may be present in the tibial bone anchoring component 116, with greater porosity on the bone-facing side 136, and lesser porosity on the joint-facing side 134. If desired, the joint-facing side 134 may be made substantially nonporous to enhance adhesion to the tibial articulating component 114, and the bone-facing side 136 may have a high level of porosity to promote bone in-growth.

As shown, the bone-facing side 132 of the tibial articulating component 114 may have a central plateau 400 that extends toward the tibial bone anchoring component 116, and a peripheral recess 402 that encircles the central plateau 400 and is recessed from the tibial bone anchoring component 116. The joint-facing side 134 of the tibial bone anchoring component 116 may have a shape that is complementary to that of the bone-facing side 132 of the tibial articulating component 114. Specifically, the joint-facing side 134 may have a peripheral ridge 410 that encircles an interior recess 412. An alcove 414 may extend into the peripheral ridge 410, from the space above the interior recess 412. When the tibial articulating component 114 and the tibial bone anchoring component 116 are assembled together, the central plateau 400 may be received within the interior recess 412, and the peripheral ridge 410 may engage the central plateau 400.

In some embodiments, the tibial articulating component 114 and the tibial bone anchoring component 116 may be secured together by the same bonding process described above in connection with the femoral articulating component 110 and the femoral bone anchoring component 112 of the femoral prosthesis 102, or with a modified version of such a bonding process. Thus, FIG. 4 depicts the exemplary application of the paste 240 to the interior recess 412 of the joint-facing side 134 of the tibial bone anchoring component 116.

Figure 5:
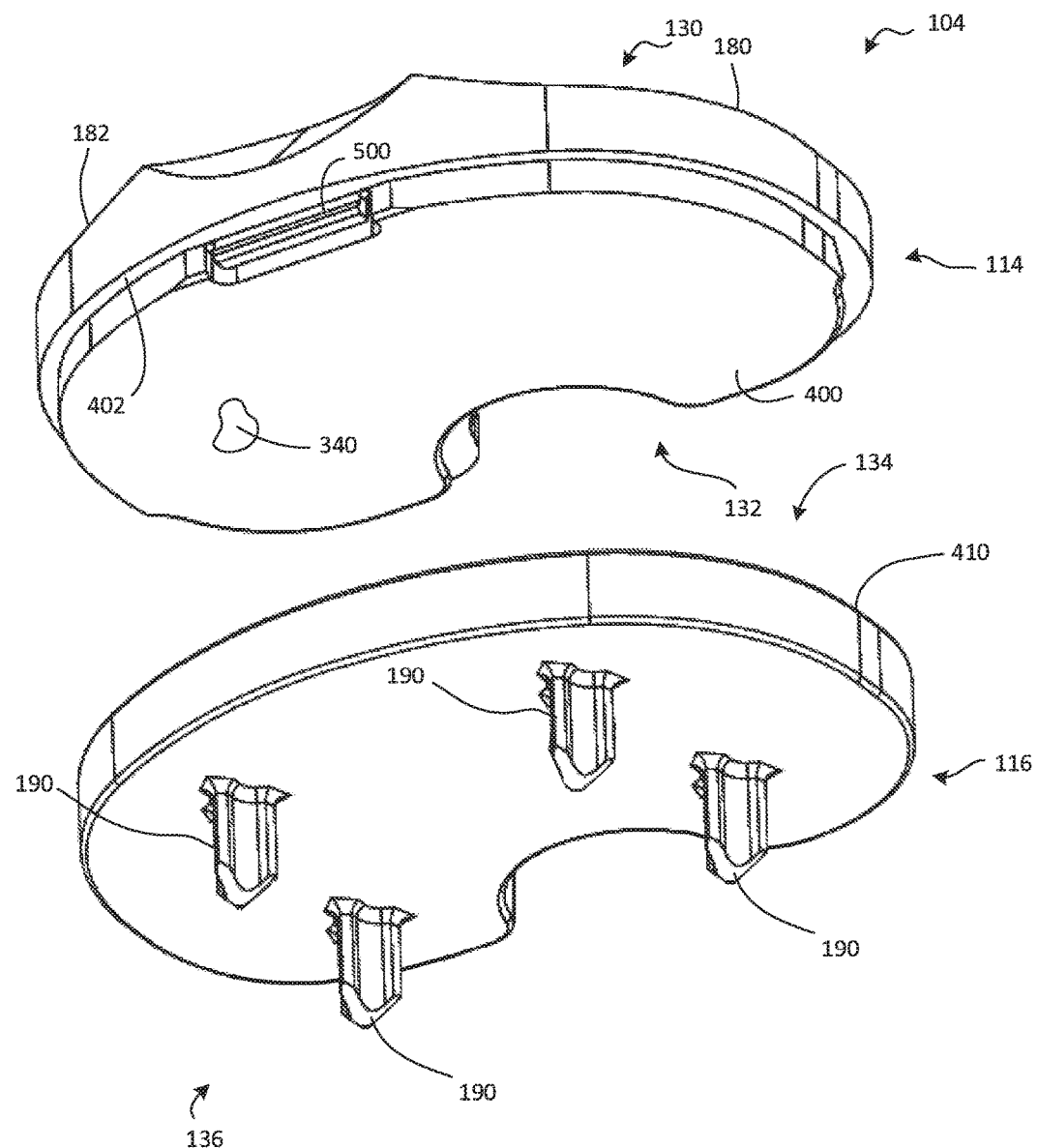
FIG. 5 is an exploded, perspective view, from a different viewpoint, of the tibial prosthesis of the knee arthroplasty system of FIG. 1.

FIG. 5 is an exploded, perspective view, from a different viewpoint, of the tibial prosthesis 104 of the system 100 of FIG. 1. As shown, the central plateau 400 of the bone-facing side 132 of the tibial articulating component 114 may have a lip 500 that protrudes anteriorly. When the tibial articulating component 114 and the tibial bone anchoring component 116 are assembled, the lip 500 may protrude into the alcove 414 depicted in FIG. 4. Engagement of the lip 500 and the alcove 414 may further help to hold the anterior portions of the tibial articulating component 114 and the tibial bone anchoring component 116 together.

FIG. 5 also depicts the bone-facing side 136 of the tibial bone anchoring component 116 in greater detail. Four of the posts 190 may be present on the bone-facing side 136, and may help enhance the level of engagement of the bone-facing side 136 with the underlying bone, and in particular, with the cortical bone at the proximal end of the tibia. The posts 190 may also increase the surface area of the bone-facing side 136 in contact with the bone of the tibia, thereby further enhancing the potential for bone cement bonding and/or bone in-growth between the tibia and the bone-facing side 136.

Further, if desired, the tibial bone anchoring component 116 may be processed as described above in the description of the femoral bone anchoring component 112, such that the tibial bone anchoring component 116 has a surface layer 230 formed of Titanium Dioxide nanotubes. Such a surface layer 230 may further enhance bone in-growth to further secure the bone-facing side 136 to the bone of the tibia.

As mentioned previously, the tibial articulating component 114 and the tibial bone anchoring component 116 may be secured together through the use of a method like that set forth in the description of the femoral articulating component 110 and the femoral bone anchoring component 112. In the course of such a method, the paste 240 may be applied to the bone-facing side 132 of the tibial articulating component 114 and/or to the joint-facing side 134 of the tibial bone anchoring component 116.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

While specific embodiments and applications of the present disclosure have been illustrated and described, it is to be understood that the scope of the appended claims is not limited to the precise configuration and components disclosed herein. Various modifications, changes, and variations which will be apparent to those skilled in the art may be made in the arrangement, operation, and details of the methods and systems disclosed herein.

What is claimed is:

1. A method for manufacturing a prosthesis for replacing an articular surface on a bone, the method comprising:
    casting an articulating component comprising:
        an articulating component joint-facing side comprising an articular surface; and
        an articulating component bone-facing side comprising a bone-facing shape; and
    fabricating a bone anchoring component with a porous structure, comprising:
        a bone anchoring component joint-facing side comprising a joint-facing shape that is complementary to the bone-facing shape; and
        a bone anchoring component bone-facing side comprising a bone engagement surface having a porous structure with pores selected to facilitate in-growth of the bone into the pores; and
    securing the bone anchoring component joint-facing side to the articulating component bone-facing side by:
        applying Titanium-based nanoparticles between the articulating component bone-facing side and the bone anchoring component joint-facing side; and
        heating the Titanium-based nanoparticles to a temperature sufficient to melt the Titanium-based nanoparticles, but insufficient to melt the articulating component or bone anchoring component.

2. The method of claim 1, wherein fabricating the bone anchoring component comprises direct metal laser sintering Titanium to form a porous structure.

3. The method of claim 1, further comprising anodizing the bone anchoring component to form a surface layer of Titanium Dioxide nanotubes on the bone anchoring component joint-facing side.

4. The method of claim 3, further comprising heating the bone anchoring component to a temperature sufficient to change at least a portion of the surface layer of Titanium Dioxide nanotubes to anatase.

5. The method of claim 1, wherein:
    casting the articulating component comprises casting the articulating component from an alloy of Cobalt Chromium to establish one or more crystalline structures of the alloy of Cobalt Chromium; and
    heating the Titanium-based nanoparticles to the temperature comprises heating at least part of the bone anchoring component and at least part of the articulating component to a bonding temperature below melting temperatures of Cobalt and Chromium, so as to leave the crystalline structures intact.

6. The method of claim 5, wherein heating the Titanium-based nanoparticles comprises:
    placing the articulating component, the bone anchoring component, and the Titanium-based nanoparticles in a furnace; and
    in the furnace, heating the articulating component, the bone anchoring component, and the Titanium-based nanoparticles to the temperature.

7. The method of claim 5, wherein heating at least part of the bone anchoring component and part of the articulating component to the bonding temperature comprises laser welding a perimeter and/or seams of the bone anchoring component joint-facing side and the articulating component bone-facing side together.

8. The method of claim 5, further comprising, prior to heating at least part of the bone anchoring component and part of the articulating component to the bonding temperature, applying a paste to one or both of the bone anchoring component joint-facing side and the articulating component bone-facing side, the paste comprising the Titanium-based nanoparticles and a gelatin and/or a glycerin.

9. The method of claim 8, further comprising, after applying the paste on one or both of the bone anchoring component joint-facing side and the articulating component bone-facing side, and prior to heating at least the bone anchoring component joint-facing side and the articulating component bone-facing side to the bonding temperature:
    assembling the articulating component and the bone anchoring component such that the paste is sandwiched between the bone anchoring component joint-facing side and the articulating component bone-facing side; and
    pressing the bone anchoring component joint-facing side and the articulating component bone-facing side together.

10. The method of claim 9, wherein heating at least the bone anchoring component joint-facing side and the articulating component bone-facing side to the bonding temperature comprises, with the bone anchoring component joint-facing side and the articulating component bone-facing side pressed together, heating at least the bone anchoring component joint-facing side and the articulating component bone-facing side to 500° C. to debind the gelatin and/or glycerin and melt the Titanium-based nanoparticles.

11. A method for manufacturing a prosthesis for replacing an articular surface on a bone, the method comprising:
   casting metals comprising at least Cobalt and Chromium to form an articulating component comprising:
      an articulating component joint-facing side comprising an articular surface; and
      an articulating component bone-facing side comprising a bone-facing shape; and
   direct metal laser sintering Titanium to form a bone anchoring component comprising:
      a bone anchoring component joint-facing side comprising a joint-facing shape that is complementary to the bone-facing shape; and
      a bone anchoring component bone-facing side comprising a bone engagement surface having a porous structure with pores selected to facilitate in-growth of the bone into the pores;
   applying a paste containing flake-shaped Titanium-based nanoparticles produced via ball milling to at least one of the bone anchoring component joint-facing side and the articulating component bone-facing side;
   assembling the articulating component and the bone anchoring component such that the paste is sandwiched between the bone anchoring component joint-facing side and the articulating component bone-facing side; and
   heating the paste to a bonding temperature sufficient to commence melting of the Titanium-based nanoparticles to secure the bone anchoring component joint-facing side to the articulating component bone-facing side.

12. The method of claim 11, further comprising:
   anodizing the bone anchoring component to form a surface layer of Titanium Dioxide nanotubes on the bone anchoring component joint-facing side; and
   after assembling the articulating component and the bone anchoring component, pressing the articulating component and the bone anchoring component together;
   wherein:
      the paste further comprises a gelatin and/or a glycerin; and
      heating the paste to the bonding temperature comprises, with the articulating component and the bone anchoring component pressed together, heating at least the bone anchoring component joint-facing side and the articulating component to a temperature sufficient to debind the gelatin and/or glycerin, melt the Titanium-based nanoparticles, and changing at least a portion of the surface layer of Titanium Dioxide nanotubes to anatase.

* * * * *